(12) United States Patent
Clavel et al.

(10) Patent No.: US 9,822,090 B2
(45) Date of Patent: Nov. 21, 2017

(54) METHOD FOR PRODUCING NEBIVOLOL HYDROCHLORIDE OF HIGH PURITY

(71) Applicant: CORDON PHARMA INTERNATIONAL GmbH, Plankstadt (DE)

(72) Inventors: Alexandre Clavel, Dijon (FR); Ilia Freifeld, Bad Vilbel (DE); Gerhard Jas, Berlin (DE); Kurt Kesseler, Hofheim (DE)

(73) Assignee: CORDEN PHARMA INTERNATIONAL GMBH, Plankstadt (DE)

( * ) Notice: Subject to any disclaimer, the term of this patent is extended or adjusted under 35 U.S.C. 154(b) by 0 days.

(21) Appl. No.: 15/118,483

(22) PCT Filed: Feb. 13, 2015

(86) PCT No.: PCT/EP2015/053160
§ 371 (c)(1),
(2) Date: Aug. 12, 2016

(87) PCT Pub. No.: WO2015/121452
PCT Pub. Date: Aug. 20, 2015

(65) Prior Publication Data
US 2017/0183323 A1   Jun. 29, 2017

(30) Foreign Application Priority Data
Feb. 14, 2014  (EP) .................................. 14155300

(51) Int. Cl.
*C07D 311/58* (2006.01)

(52) U.S. Cl.
CPC .................................. *C07D 311/58* (2013.01)

(58) Field of Classification Search
CPC ...................................................... C07D 311/58
See application file for complete search history.

(56) References Cited

U.S. PATENT DOCUMENTS

| | | |
|---|---|---|
| 2007/0021623 A1* | 1/2007 | Parthasaradhi Reddy .................. C07D 311/58 549/403 |
| 2011/0207948 A1 | 8/2011 | Maragni et al. |
| 2013/0005001 A1 | 1/2013 | Jas et al. |

FOREIGN PATENT DOCUMENTS

WO   WO 2006/016376   2/2006

* cited by examiner

*Primary Examiner* — Timothy R Rozof
(74) *Attorney, Agent, or Firm* — JMB Davis Ben-David

(57) ABSTRACT

The invention relates to a process for producing Nebivolol hydrochloride, (formula I) comprising the steps of: provision of a protected Nebivolol hydrochloride of the general formula (II), with P being an amine protecting group, and hydrogenation of said protected Nebivolol hydrochloride yielding Nebivolol hydrochloride of the formula (I).

15 Claims, No Drawings

METHOD FOR PRODUCING NEBIVOLOL HYDROCHLORIDE OF HIGH PURITY

CROSS-REFERENCE TO RELATED APPLICATIONS

This is the U.S. National Stage of International Application No. PCT/EP2015/053160, filed Feb. 13, 2015, which was published in English under PCT Article 21(2), which in turn claims the benefit of EP Patent Application No. 14155300.8, filed Feb. 14, 2014.

FIELD OF THE INVENTION

The present invention relates to an improved process for the preparation of Nebivolol hydrochloride.

BACKGROUND OF THE INVENTION

The Nebivolol-hydrochloride salt of a general formula I.

(formula I)

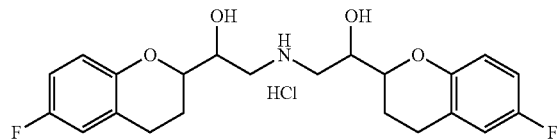

($\pm$)-[(S,R,R,R)+(R,S,S,S)-]-$\alpha,\alpha'$-[iminobis(methylene)]
bis[6-fluoro-3,4-dihydro-2H-1-benzopyran-2-methanol], (Nebivolol), is a potent and selective β1 adrenergic blocker used for treatment of high blood pressure. Nebivolol has basic properties and may be converted into its addition salts through treatment with suitable acids. Nebivolol is applied in the form of it's racemate and consists of the two enantiomers: d-nebivolol*HCl Ia and l-nebivolol*HCl Ib. The hydrochloric acid addition salt is the marketed product as disclosed in U.S. Pat. No. 4,654,362 A and its counter EP 0145067 A2.

(formula Ia)

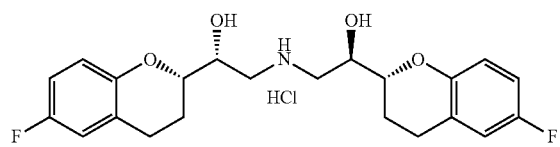

SRRR-configuration
(d-Nebivolol*HCl)

(formula Ib)

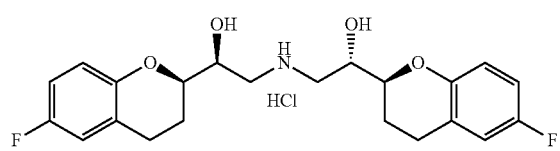

RSSS-configuration
(l-Nebivolol*HCl)

Numerous syntheses for the preparation of nebivolol hydrochloride have been disclosed, for example in U.S. Pat. No. 4,654,362 A (JANSSEN), EP 0334429 A1 (JANSSEN), WO 2004/041805 A1 (EGIS), WO 2006/016376 A1 and WO 2007/083318 A1 (HETERO DRUGS), WO 2006/025070 A2 (TORRENT), WO 2008/010022 A2 (CIMEX), WO 2008/064826 A2 and WO 2008/064827 A2 (ZACH), WO 2009/082913 A1, CN 101463024 A, WO 2010/049455 (ZACH) and WO 2010/089764 A1 (ZACH).

In general, most of the reported processes apply the reaction of two 6-fluoro-3,4-dihydro-2-oxiranyl-2H-1-benzopyran building blocks formula A

A

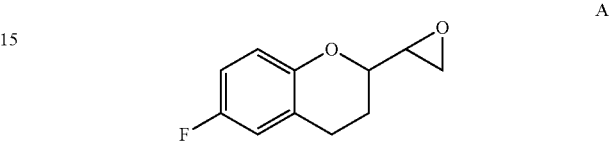

with benzyl amine. Usually, the initially resulting 6-fluoro-3,4-dihydro-2-[[(phenyl)amino]methyl]-2H-1-benzopyran-2-methanol E'

E'

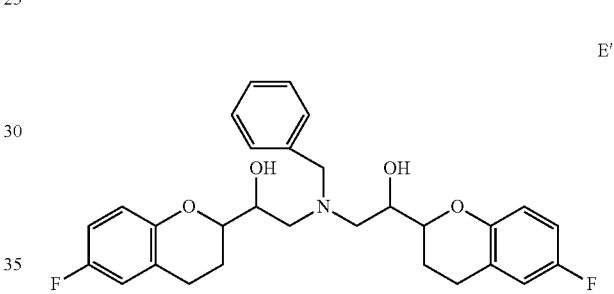

is isolated and purified before final conversion to benzyl protected nebivolol [phenylmethyliminobis(methylene)]bis[6-fluoro-3,4-dihydro-2H-1-benzopyran-2-methanol.

The patent applications WO 2006/016376 A1, WO 2007/083318 A1 and US 2009/0076288 filed by Hetero Drugs Ltd. disclose the separation of benzyl protected nebivolol by precipitation of the hydrochloride salt. The goal of those patents is the purification of benzyl-nebivolol by fractional crystallization of a crude mixture consisting of several nebivolol diastereomers.

Even if hydrochloride salt intermediates are prepared, all reported processes perform a conversion of the benzyl protected hydrochloride salt and a subsequent deprotection of benzyl protected nebivolol free base in order to get nebivolol free base. The hydrochloride salt of Nebivolol is finally prepared in the last step of the manufacturing process.

In WO 2011/091968 A1 we disclosed a highly stereoselective approach for the synthesis of racemic nebivolol (racemic mixture of d-nebivolol and l-nebivolol) as well as for the production of the individual enantiomers d-nebivolol and l-nebivolol based on enantiomerically pure chloroketones and chloroalcohols, wherein a key step of the method is a stereoselective enzymatic reduction. The hydrochloride salt of Nebivolol may be prepared in the last step of the manufacturing process.

The synthesis is performed according the general scheme 1.

Scheme 1: Synthesis of d- and l-nebivolol; PG is an ammine protecting group

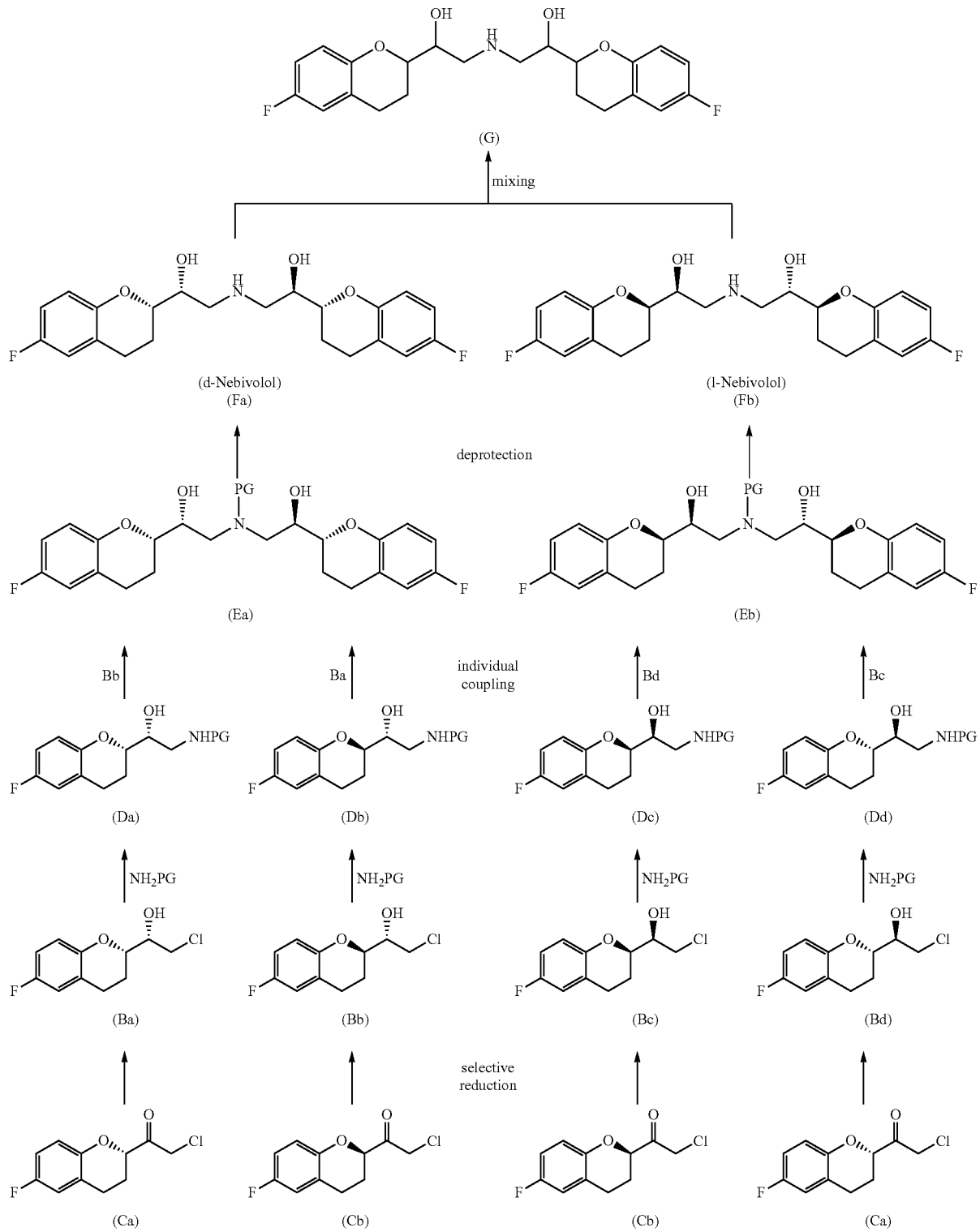

For example, d-nebivolol Fa was prepared by enzymatic reduction of 1-(2S)-(6-fluorochroman-2-yl)-2-chloroethan-1-one Ca and 1-(2R)-(6-fluorochroman-2-yl)-2-chloroethan-1-one Cb to give either the S- or the R-configurated chloroalcohol Ba or Bb. (S)-2-chloro-1-((R)-6-fluoro-3,4-dihydro-2H-chromen-2-yl)ethanol Ba was subjected to amination by treatment with sodium methoxide followed by reaction with benzylamine to give (S)-2-benzylamino-1-((R)-6-fluoro-3,4-dihydro-2H-chromen-2-yl)ethanol Da. This underwent coupling with (R)-2-chloro-1-((R)-6-fluoro- 3,4-dihydro-2H-chromen-2-yl)ethanol Bb followed by debenzylation to give d-nebivolol Fa. An analogue pathway applies if Bb was subjected to amination. l-Nebivolol Fb was produced in a similar way. Finally, d- and l-nebivolol (Fa and Fb) were mixed to give racemic nebivolol G which can be converted to the hydrochloride salt.

One of the main issues within this approach is the removal of unwanted stereoisomers of nebivolol built in the individual coupling reactions. This is caused by the fact that the starting chloroketones Ca and Cb are generally prone to epimerisation and traces of the unwanted chloroketone enantiomers can't be completely avoided in the manufacturing process and can reach levels up to 5%. These impurities lead to diastereomeric impurities in Ba-Bd and Da-Dd, and finally in Fa and Fb, too.

In consequence, the formation of unwanted nebivolol stereoisomers may need additional crystallisation steps in the last stages of the synthesis in order to remove these impurities completely to reach a content in the final product <0.1%.

WO 2010/049455 (Zach Systems) formally describes the usage of Benzyl-protected Nebivolol hydrochloride in the transfer hydrogenation (in enantiomerically pure form, see example 1, 2 in WO 2010/049455), but the hydrochloride is converted first to the free base by alkali before running the hydrogenation reaction. The transfer hydrogenation itself is carried out in the presence of formic acid which initially leads to the formation of Nebivolol formate salts. To get the hydrochloride the formate salts have to be converted to the free base first. Only after the debenzylation d-nebivolol and l-nebivolol are mixed to a racemate.

IN 2012MU02522 discloses the debenzylation of d- and l-N-Benzyl-Nebivolol Hydrochloride in presence of ammonium formate, but the resulting nebivolol formate again needs the conversion to the hydrochloride.

Mixing of d- and l-Benzyl-Nebivolol before the final deprotection step has been described in CN 102344431, CA 101463024, WO 2009/082913, EP 2236510, WO 2007/083318, and WO 2006/016376), but in neither case the hydrochloride salt has been used.

All of the before mentioned methods provide nebivolol hydrochloride with a several conversion or purification steps, which comprise naturally a loss of product during the process compared to a method using less conversion or purification steps.

The goal of the present invention is to provide an improved and economical process for preparation of nebivolol hydrochloride salt directly from its protected precursor.

SUMMARY OF THE INVENTION

According to a first aspect, the invention relates to a process for producing Nebivolol hydrochloride of formula 1,

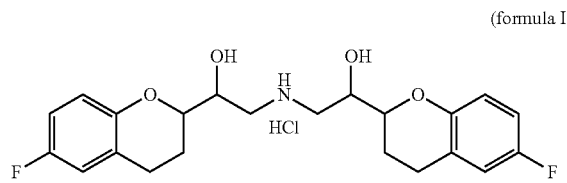

(formula I)

comprising the steps of:
a. provision of a protected Nebivolol hydrochloride of the general formula II

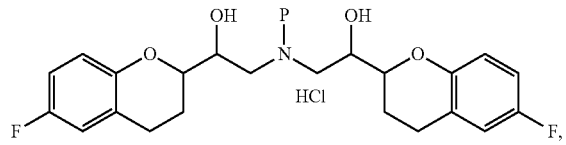

(formula II)

with P being an amine protecting group, and
b. hydrogenation of said protected Nebivolol hydrochloride of formula II yielding Nebivolol hydrochloride of the formula I.

According to a second aspect, the invention relates to a process for producing Nebivolol hydrochloride of formula I,

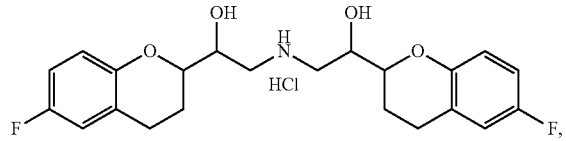

(formula I)

in particular d-Nebivolol hydrochloride or l-Nebivolol hydrochloride of the general formula Ia or Ib

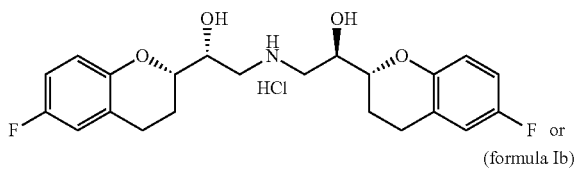

(formula Ia)

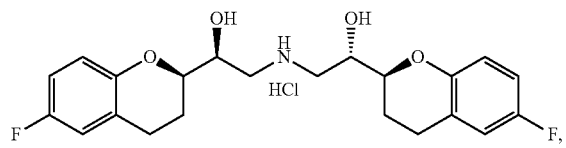

(formula Ib)

comprising the steps of:
a. activation of a carboxylic acid of a general formula VI,

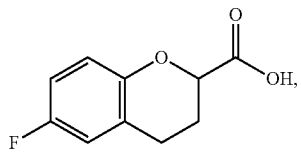

(formula VI)

in particular of the formula VIa or VIb,

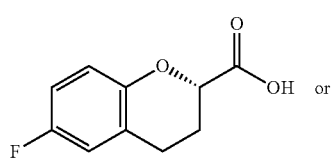

(formula VIa)

(formula VIb)

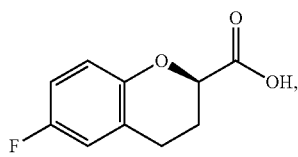

by using a peptide coupling agent, b. coupling of the activated carboxylic acid with a malonic acid derivative providing a β-ketoester precursor, c. converting the β-ketoester precursor to the ketone of the general formula VII, (formula VII)

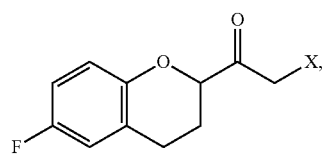

in particular of the ketone of formula VIIa or VIIb, (formula VIIa)

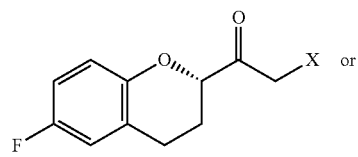

(formula VIIb)

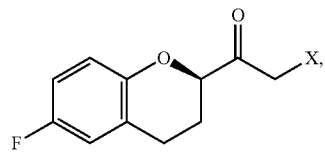

with X being Cl or Br, in particular X is Cl, d. stereoselective reduction of the ketone of the general formula VII, in particular of the ketone of formula VIIa or VIIb, providing a alcohol of the general formula IVa to IVd, (formula IVa)

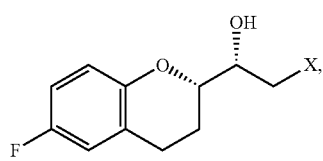

(formula IVb)

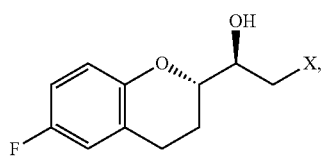

(formula IVc)

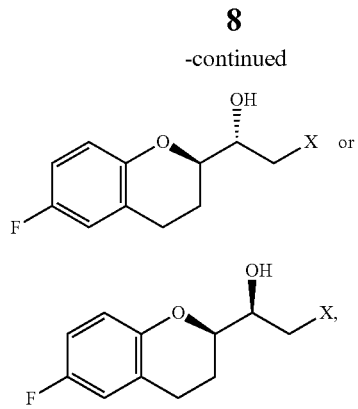

(formula IVd)

with X having the same meaning as defined above, e. provision of an protected aminoalcohol of the formula IIIa to IIIb, (formula IIIa)

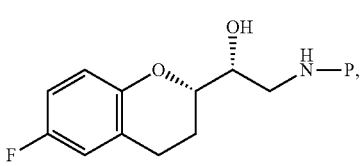

(formula IIIb)

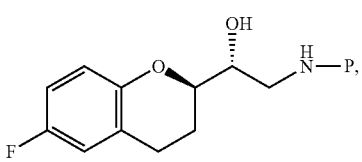

(formula IIIc)

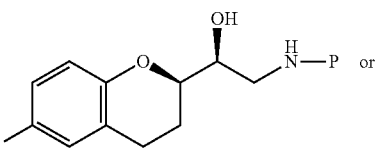

(formula IIId)

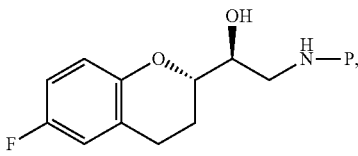

with P being an amine protecting group, derived form the alcohols of the general formula IVa to IVd, f. coupling of the aminoalcohol IIIa with the alcohol IVb or the aminoalcohol IIIb with the alcohol IVa providing protected d-nebivolol compound, or coupling of the aminoalcohol IIIc with the alcohol IVd or the aminoalcohol IIId with the alcohol IVc, providing protected l-nebivolol compound, g. treatment with hydrochloric acid, and isolation of a protected Nebivolol hydrochloride of formula II, IIa or IIb, h. hydrogenation of said protected Nebivolol hydrochloride of formula II, IIa, IIb or a mixture of IIa and IIb yielding Nebivolol hydrochloride of the formula I, Ia, Ib or a mixture of Ia and Ib.

As used herein the term "ee," refers to an enantiomeric excess of a substance. Enantiomeric excess is defined as the absolute difference between the enantiomers divided by the sum of the enatiomers and is expressed in percent. An analogue definition applies for a diastereomeric excess ("de"), also referred to as "diastereochemical purity".

A protecting group in the context of the present specification is a group employed to reduce the reactivity of a particular moiety. Protecting groups are well known to the person skilled in the art of organic chemistry. P. G. M. Wuts, "Greene's Protective Groups in Organic Synthesis,"4th ed. (2006, Wiley; ISBN 978-0-471-69754-1; 5th edition June 2013 Wiley-Blackwell).

The term "substituted" refers to the addition of a substituent group to a parent compound.

"Substituent groups" can be protected or unprotected and can be added to one available site or to many available sites in a parent compound. Substituent groups may also be further substituted with other substituent groups and may be attached directly or by a linking group such as an alkyl, an amide or hydrocarbyl group to a parent compound. "Substituent groups" amenable herein include, without limitation, halogen, oxygen, nitrogen, sulphur, hydroxyl, alkyl, alkenyl, alkynyl, acyl, carboxyl, aliphatic groups, alicyclic groups, alkoxy, substituted oxy, aryl, aralkyl, heterocyclic radical, heteroaryl, heteroarylalkyl, nitro or cyano.

DETAILED DESCRIPTION

A first aspect of the invention relates to a process for producing Nebivolol hydrochloride,

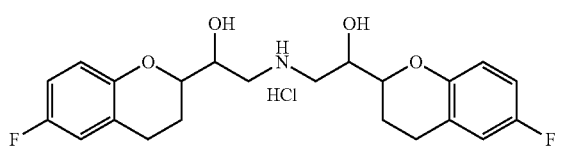
(formula I)

comprising the steps of:
a. provision of a protected Nebivolol hydrochloride of the general formula II

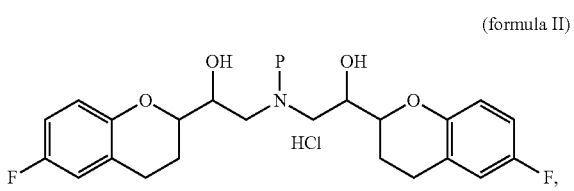
(formula II)

with P being an amine protecting group, and
b. hydrogenation of said protected Nebivolol hydrochloride of formula II yielding Nebivolol hydrochloride of the formula I.

In some embodiments,
i. a protected d-Nebivolol hydrochloride of the general formula IIa

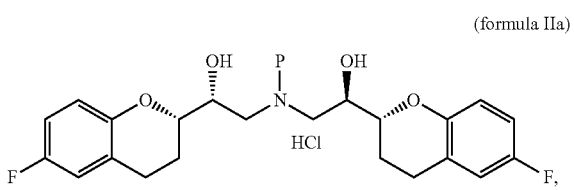
(formula IIa)

ii. a protected l-Nebivolol hydrochloride of the general formula IIb

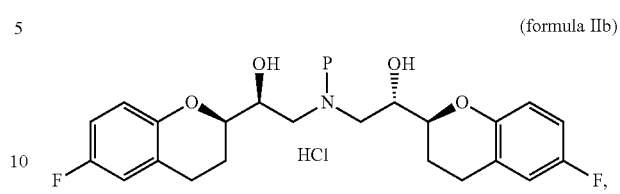
(formula IIb)

or
iii. a mixture of a protected d-Nebivolol hydrochloride and a protected l-Nebivolol hydrochloride compound,
with P being an amine protecting group,
is provided in step a, and wherein said hydrogenation of step b yields
i. the corresponding d-Nebivolol hydrochloride

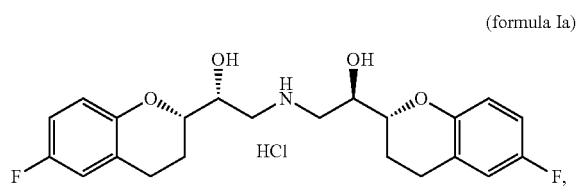 [SMILES: O[C@H](CNC[C@@H](O)[C@H]1CCc2cc(F)ccc2O1)[C@@H]1CCc2cc(F)ccc2O1 ; Cl]
(formula Ia)

ii. the corresponding l-Nebivolol hydrochloride

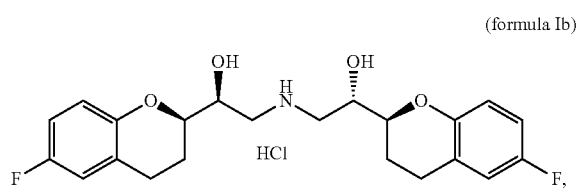 [SMILES: O[C@@H](CNC[C@H](O)[C@H]1CCc2cc(F)ccc2O1)[C@@H]1CCc2cc(F)ccc2O1 ; Cl]
(formula Ib)

or
iii. the corresponding mixture of d-Nebivolol hydrochloride and l-Nebivolol hydrochloride of formula Ia and Ib.

In some embodiments, a racemic mixture of said protected d-Nebivolol hydrochloride IIa and said protected l-Nebivolol hydrochloride IIb is provided in step a, and wherein said hydrogenation of step b yields the corresponding racemic Nebivolol hydrochloride (racemat).

Surprisingly, we have found that nebivolol of higher purity can be obtained when the product of the coupling reaction (protected Nebivolol hydrochloride of the general formula II or protected d- or l-Nebivolol hydrochloride of the general formula IIa or IIb) is isolated as hydrochloride salt and the deprotection step is carried out directly on the hydrochloride salts of said protected Nebivolol hydrochloride compounds (e.g. compounds of the general formula II, IIa, IIb or mixtures of IIa and IIb) to give the nebivolol HCl salt (of formula I, Ia or Ib or mixtures of Ia and Ib) directly.

Additionally, we have found that it is advantageous to run the deprotection with the racemic mixture of d-Nebivolol hydrochloride and l-Nebivolol hydrochloride of formula IIa and IIb, instead of preparing the racemate of Nebivolol hydrochloride in the last step.

This process of the invention has the advantage that no interim or final recrystallization step is needed to get nebivolol hydrochloride of high purity.

The hydrogenation, particularly the transfer hydrogenation, of N-Benzyl nebivolol hydrochloride in its racemic or enantiomerically form is novel and not described in the literature yet whereas the transfer hydrogenation of the free base is well known (see for example WO 2008/064827, WO 2010/049455, IN 2012MU02522, WO 2011091968).

In some embodiments, the amine protecting group P is

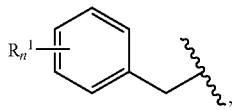

with n being 0, 1, 2, 3, 4 or 5 and each $R^1$ being selected independently from any other $R^1$ from F, Br, Cl, I or $C_1$- to $C_4$-alkyl, wherein in particular n is 0.

In some embodiments, a Pd catalyst (5-10% Pd/C) and cyclohexene is used in the hydrogenation of step b. Cyclohexene may be replaced by alkylated cylohexenes (like 1-methyl-cyclohexene) or 1,4-cyclohexadiene.

In some embodiments, compounds of the formula II, IIa, IIb or mixtures thereof are dissolved in a solvent, preferably THF/water mixture (8:1 to 3:1) and treated with 5-10% Pd/C (5-10% w/w) under reflux in the presence of 50-100% w/w cyclohexene, subsequently a hot filtering of the solution is applied to remove the catalyst and crystallisation by cooling to 0° C. yields the product.

In some embodiments, a mixture of said protected d-Nebivolol hydrochloride IIa and said protected l-Nebivolol hydrochloride IIb is provided by dissolving $n_{dp}$ mole of said protected d-Nebivolol hydrochloride IIa and $n_{lp}$ mole of said protected l-Nebivolol hydrochloride IIb in a precipitation solvent and a subsequent precipitation of said mixture, wherein $n_{dp}$ is the molar amount of said protected d-Nebivolol hydrochloride IIa and $n_{lp}$ is the molar amount of said protected l-Nebivolol hydrochloride IIb.

In general, any ratio of $n_{dp}$ to $n_{lp}$ can be used. Preferably a ratio near a racemic mixture, more preferably a racemic mixture, may be applied. For example, $n_{dp}$ to $n_{lp}$ may be 60:40, 60:50, 50:60 or 40:60.

In some embodiments, the difference between the used amount of d-Nebivolol hydrochloride Ia and l-Nebivolol hydrochloride Ib may be approximately 20% (eg. 1 mol d-Nebivolol hydrochloride and 0.8 mole l-Nebivolol hydrochloride respectively 1.2 mole l-Nebivolol hydrochloride is used). In some embodiments, the difference between the used amount of d-Nebivolol hydrochloride and l-Nebivolol hydrochloride may be approximately 10%.

In some embodiments, a racemic mixture of said protected d-Nebivolol hydrochloride IIa and said protected l-Nebivolol hydrochloride IIb is provided by dissolving 1 mole of said protected d-Nebivolol hydrochloride IIa and 1 mole of said protected l-Nebivolol hydrochloride IIb in a precipitation solvent and a subsequent precipitation of said racemic mixture.

In some embodiments, the precipitation solvent is a THF/water mixture.

In some embodiments, the protected Nebivolol hydrochloride IIa and IIb is provided by mixing and dissolving of the protected Nebivolol hydrochloride IIa and IIb in equimolar amounts in 8:1 to 3:1 THF/water mixture and crystallisation at 0° C. followed by filtration.

In some embodiments, the protected d-Nebivolol hydrochloride IIa and the protected l-Nebivolol hydrochloride IIb is provided by a. a coupling reaction of
 i. aminoalcohols of the general formula IIIa to IIId

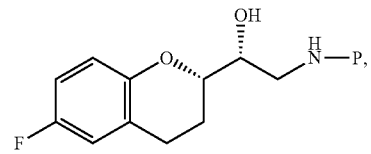
(formula IIIa)

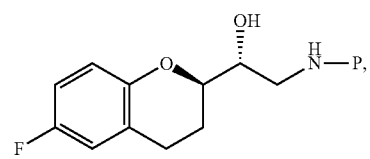
(formula IIIb)

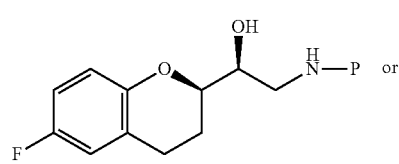
(formula IIIc)

or

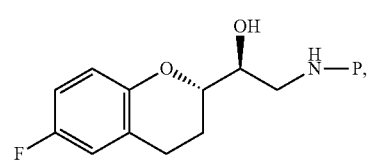
(formula IIId)

with P being an amine protecting group as defined previously,
 ii. with chloroalcohols of the general formula IVa to IVd

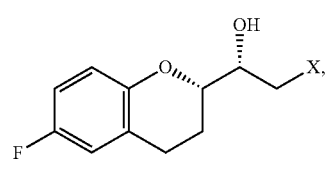
(formula IVa)

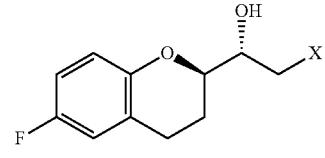
(formula IVb)

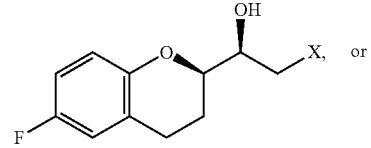
(formula IVc)

or

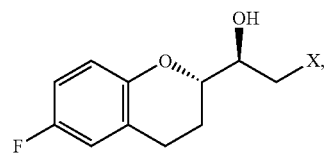
(formula IVd)

with X being a leaving group, in particular X is selected from Cl, Br, I, OSO₂R or OSO₂Ar,
with R being a $C_1$ to $C_6$-Alkyl, preferably methyl and Ar being an aromatic moiety, in particular phenyl, 4-nitrophenyl, tolyl or similar moieties thereto.

providing a protected d-Nebivolol compound and a protected l-Nebivolol compound, which are produced by a coupling reaction of compound IIIa with compound IVb or compound IIIb with compound IVa and a coupling reaction of compound IIIc with compound IVd or compound IIId with compound IVc, and b. a subsequent treatment of said protected d-Nebivolol compound and said protected l-Nebivolol compounds with hydrochloric acid.

The starting enantiomerically pure chloroalcohols IVa-IVd can be prepared from chiral 6-fluoro chromatic acid via chiral chloroketones according to known techniques as for example described in WO 2011/091968 and DE 10 2010 005 953. In order to get chloroketones and subsequently compounds IV of high enantiomerical purity we have developed a new access to chloroketones which is described in the second aspect of the invention.

In some embodiments, the aminoalcohols IIIa to IIId are provided by converting said chloroalcohols IVa to IVd to epoxide intermediates of the general formula Va to Vd

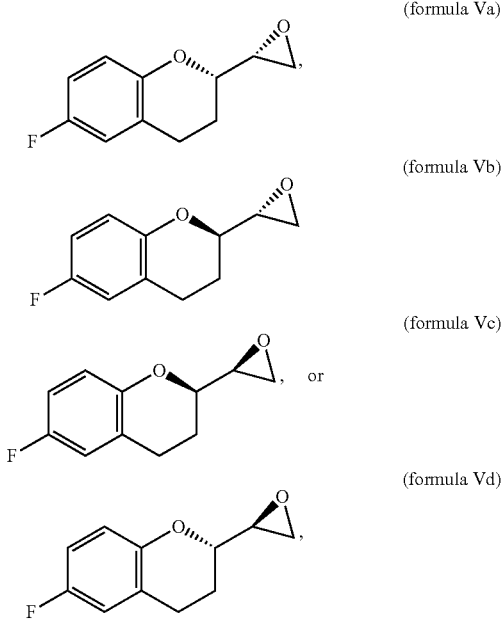

and a subsequent treatment with an amine of the formula HNP, with P being an amine protecting group as defined previously, wherein in particular said epoxide intermediates Va to Vd are not isolated prior to said treatment with the amine of the formula HNP.

In some embodiments, the coupling reaction of said aminoalcohols IIIa to IIId with said chloroalcohols IVa to IVd is achieved by a conversion of said chloroalcohols IVa to IVd to said epoxide intermediates Va to Vd and a subsequent coupling with said aminoalcohols IIIa to IIId, wherein in particular said epoxide intermediates Va to Vd are not isolated prior to said coupling with said aminoalcohols IIIa to IIId.

In some embodiments, the conversion of the chloroalcohols IVa to IVd is achieved by a base, in particular an alkoxide, tertiary amines or inorganic bases like carbonates or bicarbonates and hydroxides, in a protic organic solvent, in particular in alcohols, more preferably in isopropanol.

In some embodiments, the amine of the formula HNP is benzylamine, wherein in particular the treatment of said epoxide intermediates Va to Vd for providing said aminoalcohols IIIa to IIId comprises the addition of 1-10 eq of benzylamine.

In some embodiments, the amine of the formula HNP is benzylamine, wherein in particular the treatment of said epoxide intermediates Va to Vd for providing said aminoalcohols IIIa to IIId comprises the addition of 10 eq of benzylamine.

Compounds IVa-IVd are dissolved in isopropanol and treated with a stoichiometric equivalent of a base (for example sodium methoxide in methanol) to yield the corresponding epoxides V which are not isolated and kept in solution. The interim epoxides are subjected to reaction with excess benzylamine (2-10 eq) at 80° C. After removal of excess benzylamine the crude mixture is treated with isopropanol/water to yield the enantiomerically pure compounds IIIa-IIId, which are isolated and purified by precipitation at 0° C. (80-85% yield).

Generally, benzylamine may be replaced by substituted benzylamines containing additional alkyl groups and/or halogen atoms.

By cross-coupling reaction of IIIa with IVb (or IIIb with IVa) at 80° C. in isopropanol as solvent and IIIc with IVd (or IIId with IVc)—again by conversion of IVa-IVd to the epoxides Va-Vd first—compounds IIa and IIb are directly obtained by precipitation after treatment with HCl during the work-up procedure (the free bases are not isolated).

The enantiomerically pure hydrochlorides IIa and IIb are mixed in an equimolar mixture in a THF/water-mixture at ambient temperature. The racemate is gained by crystallisation in about 95% yield after aging the mixture and cooling to 0° C. in a purity >99.5%. It has to be noted that it is not necessary to mix the hydrochlorides IIa and IIb in equimolar ratio, as discussed above, because of the unique crystallisation behaviour of the racemate which apparently is similar to that reported for racemic Nebivolol hydrochloride (see Tuchalski et al: *Journal of Molecular Structure* 800 (1-3), 2006, 28-44). Even if one enantiomer is present in significant excess (10-20%) a perfect racemate is obtained by crystallisation. This unique crystallisation behaviour also leads to almost complete removal of all unwanted isomers of nebivolol that can be produced due to diasteromeric impurities present in starting materials IIIa-IIId.

Finally, racemic N-benzyl-protected Nebivolol can be obtained as HCl salt under transfer hydrogenation conditions from II (or IIa, IIb or a mixture, in particular a racemic mixture, thereof) using Pd/C as catalyst and cyclohexene as hydrogen donor in THF/water mixture. Whereas the hydrogenation of the hydrochloride salt gives complete conversion within 2-3 hrs the deprotection of the free base results in only 10% conversion. After treatment with isopropylacetate racemic Nebivolol of high purity is obtained.

The overall synthesis is illustrated in scheme 2, wherein racemic Nebivolol is depicted with the formula I.

Additionally, by precipitation of the coupling products (protected nebivolol compounds) as hydrochloride (IIa and IIb or a mixture thereof) salt during workup all unwanted isomers of nebivolol that can be produced due to impurities in starting materials IIIa-IIId are removed on the earliest step.

Transfer hydrogenation of the racemate as hydrochloride yields in a very fast reaction to highly pure racemic nebivolol*HCl without showing significant defluorination reaction as potential side reaction.

An overview of the synthesis is depicted in scheme 2.
Scheme 2: Overall Synthesis
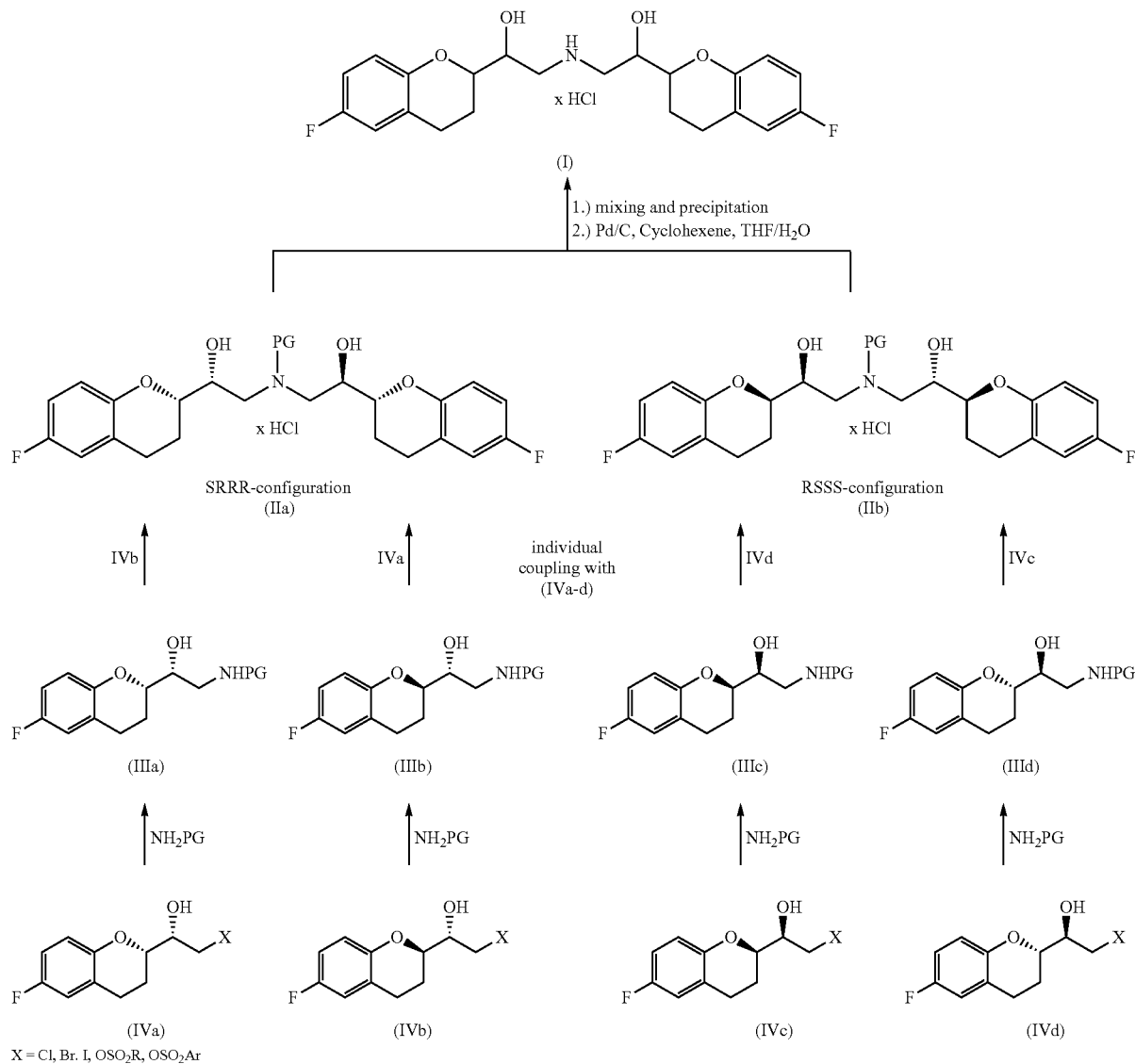
A second aspect of the invention relates to a process for producing Nebivolol hydrochloride of formula I,
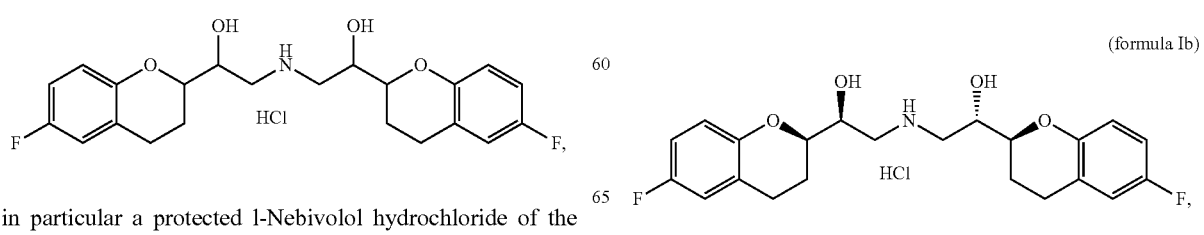
in particular a protected l-Nebivolol hydrochloride of the general formula IIa or IIb comprising the steps of:

a. activation of a carboxylic acid of a general formula VI,

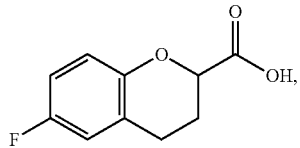
(formula VI)

in particular of the formula VIa or VIb,

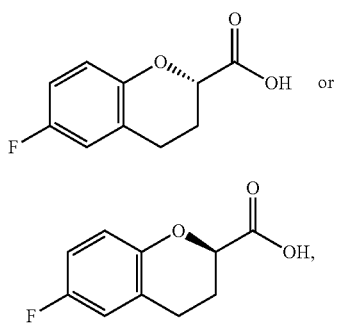
(formula VIa)

or (formula VIb)

by using a peptide coupling agent, b. coupling of the activated carboxylic acid with a malonic acid derivative providing a β-ketoester precursor, c. converting the β-ketoester precursor to the ketone of the general formula VII,

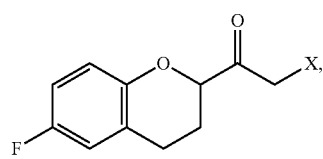
(formula VII)

in particular of the ketone of formula VIIa or VIIb,

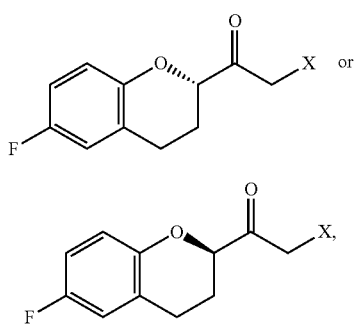
(formula VIIa)

or (formula VIIb)

with X being Cl or Br, in particular X is Cl, d. reduction of the ketone of the general formula VII, in particular of the ketone of formula VIIa or VIIb, providing a alcohol of the general formula IVa to IVd,

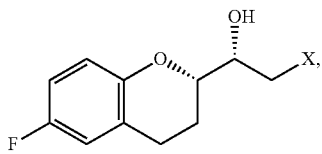
(formula IVa)

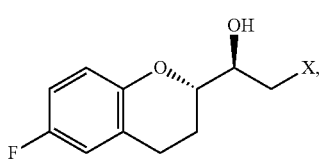
(formula IVb)

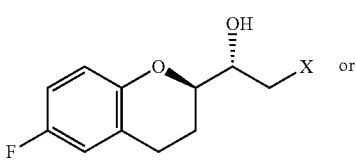
(formula IVc) or

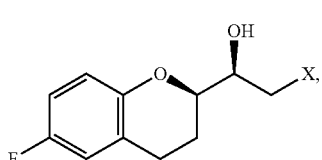
(formula IVd)

with X having the same meaning as defined above, e. provision of an protected aminoalcohol of the formula IIIa to IIIb,

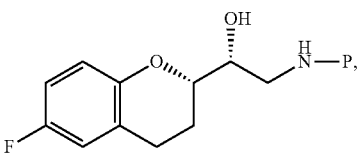
(formula IIIa)

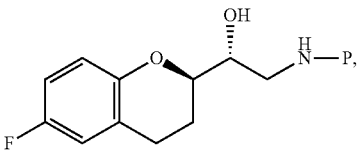
(formula IIIb)

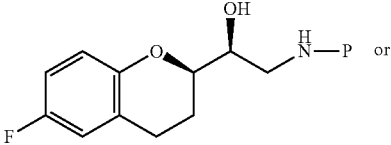
(formula IIIc) or

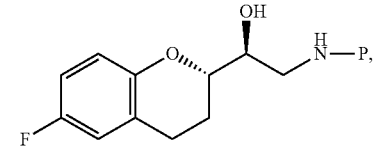
(formula IIId)

with P being an amine protecting group, derived form the alcohols of the general formula IVa to IVd, f. coupling of the aminoalcohol IIIa with the alcohol IVb or the aminoalcohol IIIb with the alcohol IVa providing protected d-nebivolol compound, or coupling of the aminoalcohol IIIc with the alcohol IVd or the aminoalcohol IIId with the alcohol IVc, providing protected l-nebivolol compound, g. treatment with hydrochloric acid, and isolation of a protected Nebivolol hydrochloride of formula II, IIa or IIb, h. hydrogenation of said protected Nebivolol hydrochloride of formula II, IIa, IIb or a mixture of IIa and IIb yielding Nebivolol hydrochloride of the formula I, Ia, Ib or a mixture of Ia and Ib.

Concerning the steps d, e, f and g reference is made to the detailed description in the WO 2011/091968 A1 (in particular the examples 1 to 12 on page 15 to 21). The same conditions and reagents are applied in the above mentioned process of the tenth aspect of the invention. A stereospecific, enzymatic reduction as disclosed in WO 2011/091968 A1 (in particular section [00028] to [00030], [00034] to [00039]. The acidic ring-opening with subsequent esterification to the final β-ketoester is disclosed in EP 1803715 A1, in particular in section [0097] to [0110]. A chlorination using $SO_2Cl_2$ followed by acid induced decarboxylation can be carried out as described in EP 1803715 A1 section [0116] to [0119].

In some embodiments, the coupling of the activated carboxylic acid with a malonic acid derivative provides a β-ketoester precursor, in particular a β-ketoester precursor of the general formula VIIIa or VIIIb,

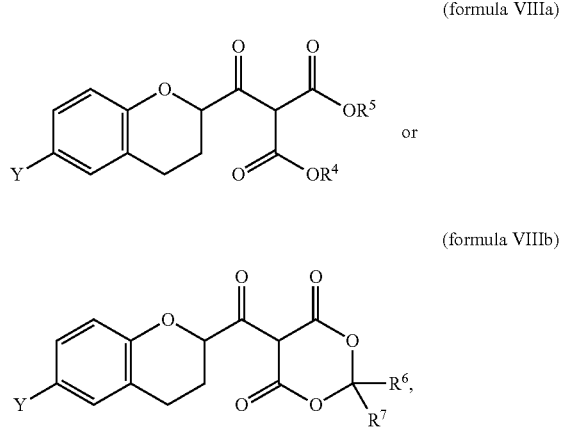

(formula VIIIa)

or (formula VIIIb)

with $R^4$ being H or $C_1$ to $C_6$ alkyl, $R^5$ being $C_1$ to $C_6$ alkyl, $R^6$ being H or $C_1$ to $C_6$ alkyl and $R^7$ being $C_1$ to $C_6$ alkyl or a substituted or unsubstituted phenyl, in particular $R^6$ being $C_1$ to $C_3$ alkyl and $R^7$ being $C_1$ to $C_3$ alkyl.

Peptide coupling agents achieve a conversion of chromatic acids to chloroketones in a high yield and purity. The use of peptide coupling agents allows a formation of the interim β-ketoester under neutral or even acidic conditions, thus, reducing the isomerisation substantially. Since the chemistry related to peptide coupling completely avoids the usage of bases it provides a solution to the substantial isomerisation occurring in the known routes.

In some embodiments, the malonic acid derivative is a malonic diester of the formula $R^4$—O—C(=O)—$CH_2$—C(=O)—O—$R^{5'}$ with $R^4$ being a $C_1$ to $C_6$ alkyl and $R^5$ being a $C_1$ to $C_6$ alkyl, or a malonic acid derivative of a formula IX

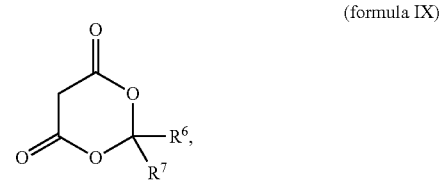

(formula IX)

with $R^6$ being $C_1$ to $C_6$ alkyl and $R^7$ being $C_1$ to $C_6$ alkyl or a substituted or unsubstituted phenyl, in particular $R^6$ and $R^7$ being $C_1$ to $C_3$ alkyl, more particularly $R^6$ and $R^7$ are $C_1$ alkyl (2,2-dimethyl-1,3-dioxane-4,6-dione; Meldrum's acid) or a malonic half ester of the formula $R^4$—O—C(=O)—$CH_2$—C(=O)—O—H or its Na— and Mg salts, with $R^4$ being a $C_1$ to $C_6$ alkyl.

In some embodiments, the malonic acid derivative of step b is a malonic diester of the formula $R^4$—O—C(=O)—$CH_2$—C(=O)—O—$R^{5'}$ with $R^4$ being a $C_1$ to $C_6$ alkyl and $R^5$ being a $C_1$ to $C_6$ alkyl, providing the interim β-ketoester of the formula 6a by a coupling reaction with the activated carboxylic acid of step a.

In some embodiments, the malonic acid derivative of step b is a malonic diester the formula IX

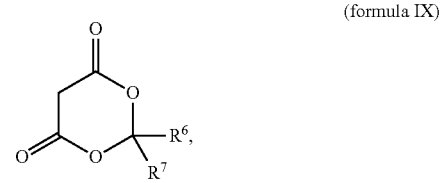

(formula IX)

with $R^6$ being $C_1$ to $C_6$ alkyl and $R^7$ being $C_1$ to $C_6$ alkyl or a substituted or unsubstituted phenyl, in particular $R^6$ and $R^7$ being $C_1$ to $C_3$ alkyl, more particularly the malonic acid derivative is 2,2-dimethyl-1,3-dioxane-4,6-dione (Meldrum's acid), providing the interim β-ketoester of the formula 5b by a coupling reaction with the activated carboxylic acid of step a.

In some embodiments, the malonic acid derivative of step b is a malonic half ester of the formula $R^4$—O—C(=O)—$CH_2$—C(=O)—O—H or its Na— and Mg salts, with $R^4$ being a $C_1$ to $C_6$ alkyl, providing the interim β-ketoester of the formula 6a by a coupling reaction with the activated carboxylic acid of step a.

In some embodiments, the activated carboxylic acid is coupled with 2,2-dimethyl-1,3-dioxane-4,6-dione (Meldrums acid) providing the meldrumate of a general formula XI

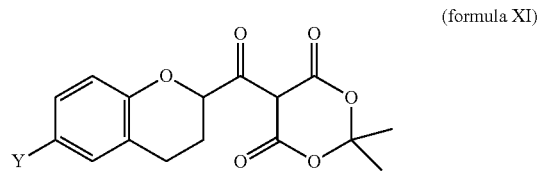

(formula XI)

as the β-ketoester precursor.

In some embodiments, the peptide coupling agent is selected from the group of triazoles, carbonylimidazoles or imminoacetates, particular the peptide coupling agent is selected from the group of carbonylimidazoles.

In some embodiments, the peptide coupling agent is selected from the group of N,N'—, 1-Hydroxybenzotriazol (HOBT), 1-Hydroxy-7-azabenzotriazol (HOAT), 1,1'-Carbonyldiimidazol (CDI), 1,1"-carbonylbis(3-methylimidazoliumtriflate) (CBMIT) or Ethylcyan(hydroxyimino)acetat (Oximapure).

In some embodiments, the coupling of the activated carboxylic acid is achieved without the presence of a base additive.

The term "base additive" comprises a base according to the definition of Brønsted and Lowry ("proton acceptor"), which is added before the coupling step b of the carboxylic acid and the malonic acid derivative with the exception of peptide coupling agents. Thus, the base additive is present during the coupling reaction. The "base additive" may also be added before the coupling step in a previous reaction step. A "base additive" according to the invention encompasses any bases which are added to the reaction mixture for any reason, in particular for the activation of the carboxylic acid derivative or in support of said activation (e.g. Diisopropylethylamine, pyridine, 2,6-lutidine, 2-chloropyridine, Na3PO4). Bases (generally weak bases) which are generated during a reaction step (e.g. in the activation step with a peptide coupling agent) of the applied reagents (e.g. peptide coupling agents, malonic acid derivatives, carboxylic acids etc.) or as side reactions of said reagents or the described reagents are not considered as "bases additives" and, thus, not excluded during the reaction step.

It has to be noted that a peptide coupling agent, as specified previously, which might be defined according to the definition of Brønsted and Lowry ("proton acceptor"), is not considered as a "base additive" according to the invention, and thus, not excluded.

In some embodiments, the coupling of the activated carboxylic acid is achieved in a reaction mixture comprising a pH in the range of 8 or less, in particular a pH in the range of 7 or less.

In some embodiments, the β-ketoester precursor of formula VIIIb, in particular the meldrumate, is converted to the ketone VII by using a β-ketoester of the general formula X

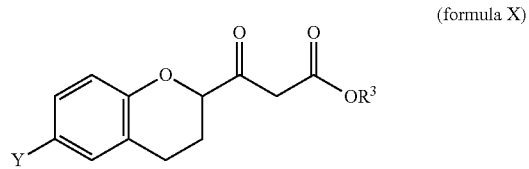

(formula X)

as an intermediate, with Y having the same meaning as defined previously, wherein the compound of the general formula X is provided by alcoholysis of the β-ketoester precursor of the general formula VIIIb, in particular by alcoholysis of the meldrumate, with an alcohol $R^3OH$, with $R^3$ being $C_1$-$C_6$ alkyl.

In some embodiments, the compound of the general formula X is halogenated, optionally hydrolyzed, and decarboxylized, to give the ketone VII.

In some embodiments, the β-ketoester precursor of formula VIIIa, in case the β-ketoester precursor derived from a reaction with a malonic half ester of the formula $R^4$—O—C(=O)—$CH_2$—C(=O)—O—H or its Na— and Mg salts, is decarboxylized to a β-ketoester of the general formula 4, subsequently halogenated and decarboxylized, to give the ketone VII, with $R^4$ having the same meaning as defined above.

In some embodiments, the chiral ketone of the general formula VIIa or VIIb is provided by using the correspondent carboxylic acids of the general formula VIa or VIb, as defined above.

The same process steps and the same reaction conditions discussed above concerning the general formula VII apply for providing chiral ketone of the general formula VIIa or VIIb using the correspondent carboxylic acids of the general formula VIa or VIb.

In some embodiments, the preparation of the ketone of the general formula VII, VIIa or VIIb is carried out as an one-pot-approach without isolation of any intermediate.

It is understood that compounds depicted as a specific enantiomer or diastereomer (eg. formula Ia, Ib, IIa, IIb, etc) and referred to as "pure" comprises said enantiomer or said diastereomer in a substantial excess, wherein the respective other possible enantiomers or diastereomers may be present in a very small amount. If not stated otherwise, said compounds comprise the highest purity possible, in which said compounds can be purchased, purified or synthesised.

The carboxylic acids of the general formula 2a or 2b is purchased in a purity of ee >99%.

EXAMPLES

Synthesis of Aminoalcohols III
General Procedure:
A reaction vessel is charged with chloro-alcohol IV (X kg), iso-propanol (5 to 8 X L) and a solution of sodium methoxide in methanol (0.6 to 0.8 X kg) is added at 20° C. The reaction mixture is aged until complete conversion of the chloroalcohols. Then, benzylamine (2 to 5 X kg) is added. The reaction mixture is heated to 80° C. and stirred until reaction completion. The reaction mixture is cooled to 0° C. in order to precipitate the desired aminoalcohol.

Example 1: Synthesis of (S,R)-aminoalcohol IIIa

According to general procedure, 34 kg of product are obtained from 33 kg of (S,S)-chloro-alcohol IVa and 153 kg of benzylamine in HPLC purity >99%.

Example 2: Synthesis of (R,S)-aminoalcohol IIIc

According to general procedure, 45 kg could be obtained from 45 kg of (R,R)-chloro-alcohol IVc and 177 kg of benzylamine in HPLC purity >99%.

Example 3: Synthesis of (S,S)-aminoalcohol IIId

According to general procedure, 68 kg could be achieved from 95 kg of (S,R)-chloro-alcohol IVd and 132 kg of benzylamine in HPLC purity >99%.

Example 4: Synthesis of (R,R)-aminoalcohol IIIb

According to general procedure, 177 g could be achieved from 260 g of (R,S)-chloro-alcohol IVb and 363 g of benzylamine in HPLC purity >99%.

Coupling Reaction
General Procedure for Benzyl Nebivolol Formation:
A reaction vessel is charged with chloroalcohol IV (X kg), iso-propanol (5 to 8 X L) and a solution of sodium methoxide in methanol (0.6 to 0.8 X kg) is added at 20° C. The reaction mixture is stirred until completion of the reaction. The appropriate aminoalcohol III (1 X kg) is added and the reaction mixture is heated to 80° C. until reaction has completed. The reaction mixture is cooled to 20° C. and aqueous hydrochloric acid (0.4 to 0.5 X kg) is added to precipitate the desired benzyl Nebivolol HCl intermediate.

Example 5: Synthesis of (R,S,S,S)-Benzyl-Nebivolol x HCl (IIb)

According to general procedure, 24 kg could be achieved from 10 kg of (S,R)-chloro-alcohol (IVd) and 10 kg of (R,S)-amino-alcohol (IIIc).

Example 6: Synthesis of (S,R,R,R)-Benzyl-Nebivolol x HCl (IIa)

According to general procedure, 28 kg could be achieved from 11 kg of (S,R)-chloro-alcohol and 11 kg of (R,S)-amino-alcohol Mixing General Procedure for Benzyl Nebivolol Mixture:

l-(R,S,S,S) Benzyl Nebivolol (0.5 X kg) IIb and d-(S,R,R,R) benzyl Nebivolol (0.5 X kg) IIa are dissolved in a mixture of tetrahydrofuran (6-8 X L) and water (1-2 X L) under a nitrogen atmosphere at room temperature. The crystallisation is initiated by aging, following cooling to 0° C. The product is isolated by filtration and the cake washed with THF.

Example 7: Racemic Benzyl Nebivolol Mixture

General procedure was applied to (R,S,S,S) and (S,R,R,R) benzyl Nebivolol free base. However, no crystalline solid was obtained.

Example 8: Racemic Benzyl Nebivolol HCl Mixture

According to general procedure, 32 kg could be achieved from 17 kg of L (R,S,S,S) benzyl Nebivolol HCl and 17 kg of D (S,R,R,R) benzyl Nebivolol HCl.

Deprotection

General Procedure for Nebivolol Deprotection:

A mixture of benzyl Nebivolol (X kg) II, tetrahydrofuran (6 to 8 X L), water (1 to 2 X L), cyclohexene (0.5 to 1 X kg) and palladium on carbon catalyst (0.05-0.10 X kg, water wet) is heated to reflux. The reaction mixture is aged until reaction completion. The palladium on carbon catalyst is removed by filtration and washed with tetrahydrofuran (1 to 2 X L). Crystallisation of the product is initiated by cooling to 0° C. The product is isolated by filtration and dried under vacuum.

Example 9: Racemic Nebivolol Free Base

General procedure was applied to dl benzyl Nebivolol free base. However, only 10% conversion was obtained with such conditions.

Example 10: Racemic Nebivolol Hydrochloride (I)

According to general procedure, 22 kg could be achieved from 29.5 kg of racemic benzyl Nebivolol HCl.

Synthesis of Pure Ketones of Formula VIIa and VIIb:

The overall process for synthesis of pure ketones, is shown, without being limited to it, in one example (Scheme 3)

Scheme 3 Example of the synthesis of pure chloroalcohols ("CLA") of formula IVa' to IVd' based on usage of either (R)- or (S)-6-fluoro-chromanic acid ("FCA") as starting material and CDI as activation reagent providing the chloroketones ("CLK") of formula VIIa' and VIIb' as intermediates. For a detailed description of the reaction conditions see examples 10 and 14.

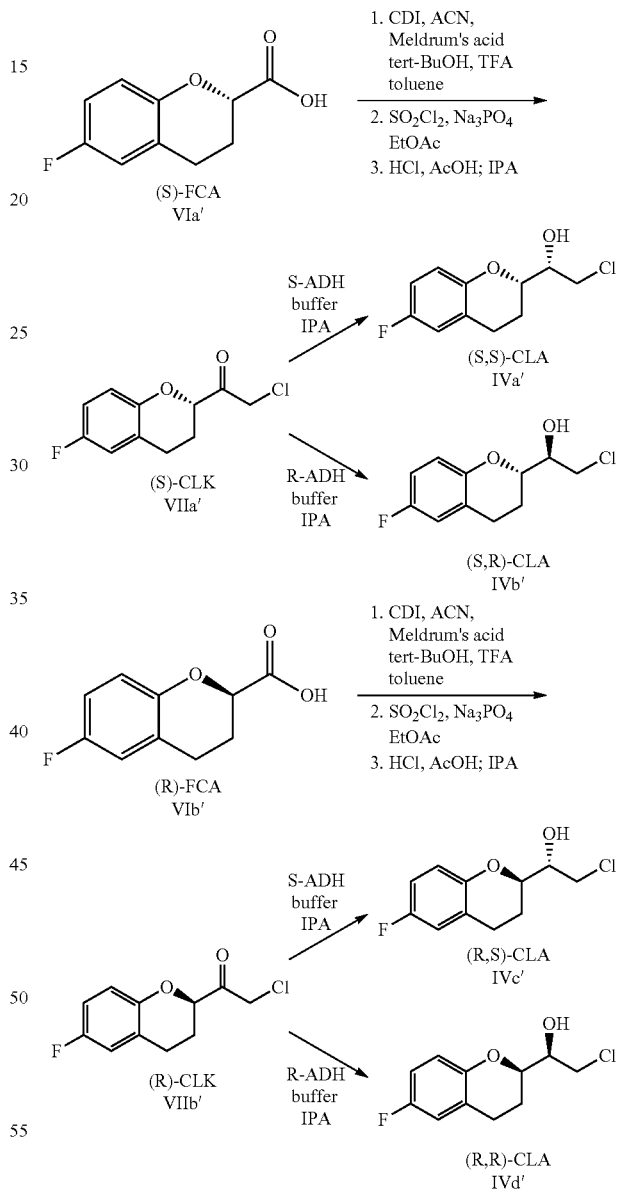

The activation of enantiomerically pure chromanic acids (ee >99%) by CDI and its conversion to the meldrumate proceeds under mild conditions at ambient temperature. Extensive HPLC and GC analysis showed that there is no racemisation on this step. Meldrum's acid gives a clean reaction with the activated chromanic acid to afford the meldrumate quantitatively. The following acidic ring-opening with subsequent esterification to the final β-ketoester also proceeded without problems and didn't induce any racemisation. Conversion of the chiral ketoesters to chiral chloroketones (and finally to chiral chloroalcohols) by first chlorination using $SO_2Cl_2$ followed by acid induced decarboxylation can be carried out as described in WO 2011/091968 A1 (see discussion above).

With the new process in hand it is possible to obtain (chloro)ketones with excellent purity (ee >98%). Overall yields of the conversion of chromanic acids to chiral (chloro)ketones are up to 80-85% which has to be considered as excellent for the whole sequence. Thus, this approach is a very effective one demonstrating its commercial and economical feasibility. Additional advantage can be taken from the fact that the synthesis of the (chloro)ketones can be carried out as one-pot process without isolation of all intermediates (see example 5).

With the new optimised process in hand the final stereospecific, enzymatic reduction of (S)- and (R)-chloroketones leads to the four chiral pure chloroalcohols using two different ADHs with yields up to 99% and diastereochemical purity >98% respectively ee up to 99.8% (see Scheme 4).

Scheme 4: Summary of the four chiral pure chloroalcohols

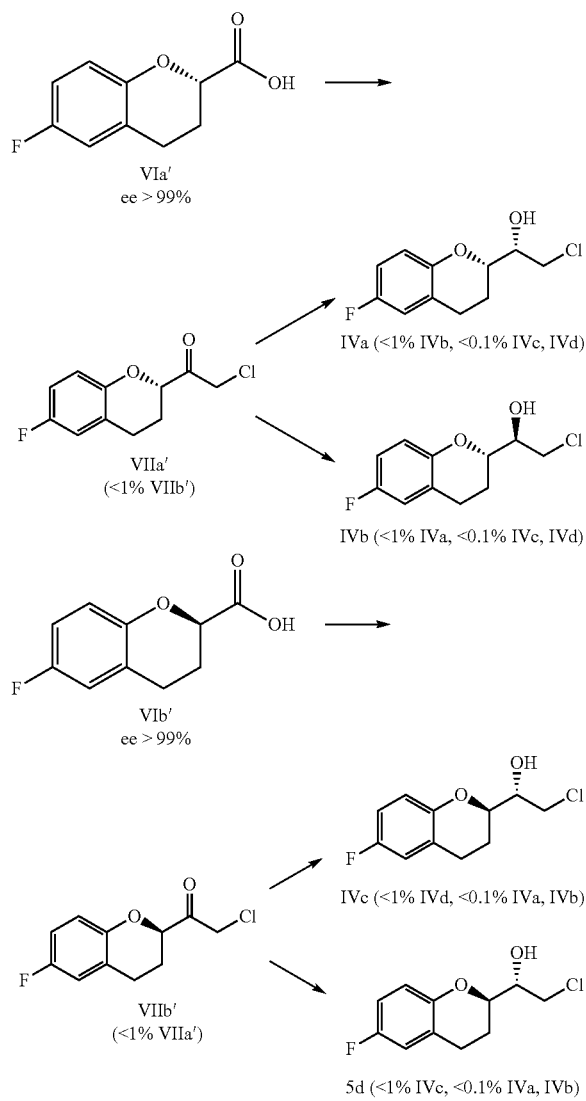

Example 10

Ent-Chloroketone Via Acid Chloride and Meldrumate:

78 g (2S)-6-Fluorochromanic acid 2a (e.e. >99%) dissolved in toluene (300 ml) and reacted with thionyl chloride (52.3 g) at 65-70° C. until complete conversion. The solvent is distilled off under vacuum. In a separate flask dichloromethane (260 ml) is charged followed by pyridine (61 ml) and Meldrum's acid (62 g). After cooling to 0-5° C. the previously prepared acid chloride is added over 3 hrs at 0° C. The resulting red brown slurry is stirred for additional 3 h min at 20-25° C. After complete conversion 1M HCl is added (121 g) and the phases are separated. The organic phase is washed twice with 1M HCl (121 g) and finally washed twice with water (120 ml). The remaining organic phase is transferred to another flask containing tert. Butanol (56 g). The mixture is heated to 70-80° C. for 6 h under continuous distillation of dichloromethane and acetone ($CO_2$ evolvement) and normal pressure. After cooling to 55-60° C. tert. butanol is added again (53 g) and the reaction mixture heated again to 80° C. until no more distillate is observed. The mixture is chilled to 20-25° C. and 1M HCl (140 g) is added. The phases are separated and the organic phase is washed twice with sat. NaHCO3 solution (148 g). The organic phase is concentrated under vacuum. The crude reaction product is transferred to a further flask and dissolved in ethyl acetate (500 ml). Na3PO4 (66 g) is added and the mixture cooled to 10-15° C. Sulfuryl chloride (61 g) is added slowly by keeping the temperature below 20° C. After complete conversion the mixture is treated with water (175 ml). The phases are separated and the organic phase treated again with water (70 ml). After phase separation the organic phase is concentrated in vacuum. The crude product is dissolved in ethyl acetate (40 ml) and mixed at ambient temperature with glacial acetic acid (291 ml) followed by 37% HCl (52 ml). The reaction mixture is heated to 40° C. for 3 h. After cooling to 20-25° C. toluene (140 ml) and water (100 ml) is added. The organic phase is washed twice with water (70 ml) and sat. NaHCO3 solution (70 ml). After additional washing with water (70 ml) the organic phase is concentrated in vacuo. The resulting crude product is treated with isopropanol (165 ml) at 20-25° C. The mixture is stirred 2 h at 0-5° C. The product is filtered off and dried to give 1a' (36 g; e.e. 93.5%) as yellow crystals.

In an analogous manner (2R)-6-fluorochromanic acid 2b can be converted to chloroketone 1b'.

Example 11

Chloroketone Preparation with PivCl and Huenig Base (2S)-6-fluorochromanic acid (11.59 kg) 2a, Meldrum's acid (9.4 kg) and DMAP (0.6 kg) are dissolved in acetonitrile (33.7 l) at 20-25° C. N-ethyl diisopropylamine (16.7 kg) is added during 20 min at 20-25° C. Pivaloyl chloride (8.0 kg) is added to the clear yellow solution over 2 h. The solution is diluted with acetonitrile (6.2 l) and stirred for additional 4-5 h at 45-50° C. Tert. butanol (16.1 kg) is added, followed by trifluoroacetic acid (10.2 kg). The mixture is heated to 50-55° C. and stirred for additional 7 h. Solvents are distilled off under vacuum and the residue is dissolved in toluene (31.4 kg) after cooling to 20-25° C. Water (23 l) is added and the phases are separated. The organic phase is washed with sat. NaHCO3 solution (23 l). The organic phase is washed again with water (23 l) and finally the solvents are distilled off to give the crude β-ketoester (19.0 kg). The product is transferred to a second vessel and dissolved in ethyl acetate (70.2 kg). Na3PO4 (9.7 kg) is added and the mixture cooled to 10° C. Sulfuryl chloride (9.0 kg) is dropped to the mixture during 2 h at 10° C. After complete conversion excess of sulfuryl chloride is hydrolysed with water (25.5 kg). The water phase is split off and discharged. The organic phase is washed with water (10.4 kg) and subsequently concentrated under vacuum to give 36.1 kg crude chlorinated β-ketoester. The crude material is treated with glacial acetic acid (42.8 kg) and 37% HCl (9.1 kg) at 20-25° C. and thereafter heated to 30-40° C. for about 7 h. After cooling to 20-25° C. toluene (17.8 kg) and water (20.4 kg) is added. After stirring for 30 min the phases are separated. The water phase is discharged and the organic phase washed twice with water (10.4 kg), sat. NaHCO3 solution (11.0 kg) and finally with water (10.4 kg). The solvents are distilled off to yield a yellow-orange-oil. Isopropanol (38.0 kg) is added and half of the solvent is distilled off. The mixture is cooled to 0-5° C. and stirred 3 h. The precipitate is filtered off to give 6.86 kg 1a (50% of theoretical yield) of 95.8% purity (HPLC) and e.e. 96.2% (determined by chiral GC).

In a similar manner (2R)-6-fluorochromanic acid 2b (10.3 kg) is converted to 1b (6.1 kg) in 50.7% yield. Purity as determined by HPLC is 96.8% with e.e 93.2% (chiral GC).

Example 12

CDI-Process:

CDI (100.7 kg) were charged in a vessel and suspended with acetonitrile (192 kg). A solution of (2R) 6-fluorochromanic acid 2a (110.7 kg) in acetonitrile (150 kg) was added over 45 min at 15-20° C. and stirred for additional 60 min until conversion has completed. A solution of Meldrum's acid (93.6 kg) in acetonitrile (97 kg) was added to the mixture at 15° C. After stirring for 12 h tert. butanol (169.5 kg) was added. The resulting mixture was cooled to 0-5° C. Trifluoroacetic acid (168 kg) was dropped to the mixture at 5° C. over 2 h and stirred for 6-7 h at 15-20° C. After complete conversion of the Meldrumate the solvent was removed by distillation. The resulting oily residue was dissolved in of toluene (279 kg) and washed with water (203 l), then twice with saturated aqueous $NaHCO_3$-solution (67 kg) and again with water (185 l). After phase separation, the aqueous layers were discarded and the toluene phase distilled off to give a slightly yellow oil which was azeotropically dried with toluene. The oily residue of (R)—FCA-β-ketoester in the reactor was dissolved in ethyl acetate (742 kg). $Na_3PO_4$ (92.5 kg) was added and the suspension transferred to a further vessel. Sulfurylchloride (87.6 kg) was added slowly at 0-5° C. over a period of 2 hours. The mixture was heated to 20° C. and stirred until completion of the reaction. Water (284 l) was added under stirring keeping the temperature below 15° C. After phase separation, the lower aqueous layer was discarded and the upper organic layer was washed water (138 l). The solvent was stripped under reduced pressure to give the (R)—FCA-α-chloro-β-ketoester as a yellow oily residue which was dissolved in glacial acetic acid (389.8 kg). Subsequently, 37% HCl (83.4 kg) was added and the mixture heated to 40° C. for 4 h. The mixture was cooled to 10° C. and 204 kg of sat. NaCl solution (204 kg) and toluene (162 kg) were added. After phase separation the organic phase was washed twice with brine (108 kg). The combined aqueous phases were re-extracted once with toluene (45 kg). Under vigorous stirring, saturated $NaHCO_3$-solution (65 l) was carefully added to the combined organic phase. After phase separation, the lower aqueous layer was discarded and the upper organic layer was washed twice with an aqueous solution of $Na_2SO_4$. Phases were separated and the organic phase concentrated under reduced pressure to yield an oily residue. Isopropanol (131 kg) was added and the residue dissolved at 40° C. A precipitate was obtained by cooling to 0° C. After additional stirring for 2 h the precipitate was filtered off. The filter cake was washed three times with ice-cold isopropanol and subsequently dried under reduced pressure. The mother liquor was reduced to the third part and crystallization was induced again by cooling to 0° C. The crystals were filtered off and both crops combined to yield 1b (92.45 kg; 71.6% of theoretical yield). Purity was 99% as determined by HPLC with e.e. 97.9% as determined by chiral GC.

Manufacturing of the corresponding (S)-chloroketone 1a was performed in the same manner.

Example 13

Conversion to Chloroalcohols (5a to 5d):
Preparation of the Buffer Solution for the Enzymatic Reduction:

Dissolve triethanolamine (4 g; 26.5 mmol) in water (215 ml). Adjust the pH of the solution, while stirring, to pH6.99 using 36% HCl (2.3 g). Add ZnCl2 (0.057 g) and fill up to 270 ml. Then add glycerol (37.5 g) and mix well.

General Procedure for the Enzymatic Reduction:

Place isopropanol (20 g) in a flask and chill with ice to 0-5° C. Add β-NAD (10 mg) and then add pre-chilled buffer solution (10 ml). Subsequently, add 50 mmol of the chloroketone at 0° C. to the reaction mixture and finally add 6,000 units (S)- or (R)-selective alcohol dehydrogenase. Warm up the sample to 20-25° C. and stir for 24 h. After conversion is complete, centrifuge the reaction solution and extract with ethyl acetate (2×10 ml) after separating the phases. Wash the organic phases with sat. NaCl solution (20 ml) and then dry over Na2SO4. The raw product is obtained through removal of the solvent by distillation in vacuum.

(S)-2-chloro-1-((R)-6-fluoro-3,4-dihydro-2H-chromen-2-yl)-ethanol 5b'

(2S)-6-Fluorochroman-2-yl-2-chloroethan-1-one 1a' and (R)-selective alcohol dehydrogenase were used in accordance with the specifications provided above to obtain 11.42 g (99% theoretical yield) 5b' (d.e. 98.3%; e.e. 99.8%).

LC-MS: m/z=230.232 (MH+, 100%)

(R)-2-chloro-1-((R)-6-fluoro-3,4-dihydro-2H-chromen-2-yl)-ethanol 5d'

In analogous manner (2R)-6-Fluorochroman-2-yl-2-chloroethan-1-one 1 b' and (R)-selective alcohol dehydrogenase were used to obtain 11.07 g (96% of theoretical yield) 5d' (d.e. 97.9%; e.e. 99.8%)

LC-MS: m/z=230.232 (MH+, 100%)

(R)-2-chloro-1-((S)-6-fluoro-3,4-dihydro-2H-chromen-2-yl)-ethanol 5c'

In analogous manner (2R)-6-Fluorochroman-2-yl-2-chloroethan-1-one 1b' and (S)-selective alcohol dehydrogenase were used to obtain 11.42 g (99% of theoretical yield) 5c' (d.e. 98.0%; e.e. 99.8%)

LC-MS: m/z=230.232 (MH+, 100%)

(S)-2-chloro-1-((S)-6-fluoro-3,4-dihydro-2H-chromen-2-yl)-ethanol 5a'

In analogous manner (2S)-6-Fluorochroman-2-yl-2-chloroethan-1-one 1a' and (S)-selective alcohol dehydrogenase were used to obtain 10.72 g (93% of theoretical yield) 5a' (d.e. 98.1%; e.e. 99.9%)

LC-MS: m/z=230.232 (MH+, 100%)

The invention claimed is:

1. A process for producing Nebivolol hydrochloride of formula I,

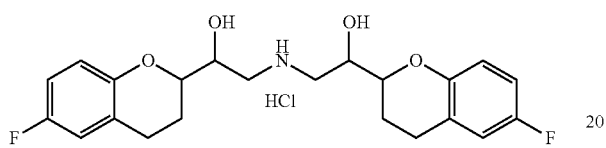
(formula I)

comprising the steps of:
a. provision of a protected Nebivolol hydrochloride of the general formula II

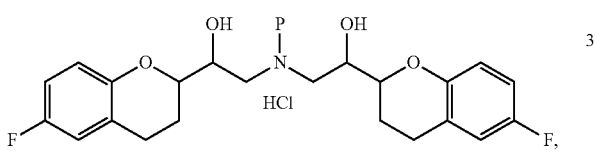
(formula II)

with P being an amine protecting group removable by hydrogenation, and
b. hydrogenation of said protected Nebivolol hydrochloride of the general formula II yielding Nebivolol hydrochloride of the formula I.

2. The process according to claim 1, wherein
i. a protected d-Nebivolol hydrochloride of the general formula IIa

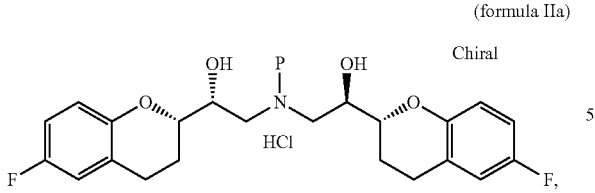
(formula IIa)

ii. a protected l-Nebivolol hydrochloride of the general formula IIb

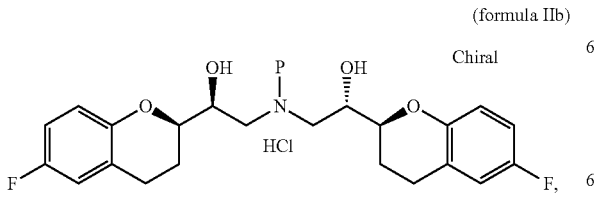
(formula IIb)

or
iii. a mixture of a protected d-Nebivolol hydrochloride of formula IIa and a protected l-Nebivolol hydrochloride of formula IIb, with P being an amine protecting group removable by hydrogenation, is provided in step a, and wherein said hydrogenation of step b yields
i. the corresponding d-Nebivolol hydrochloride

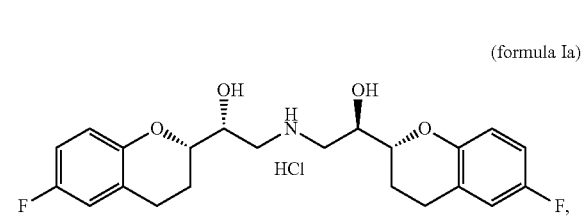 [SMILES: O[C@H](CNC[C@@H](O)[C@H]1CCc2cc(F)ccc2O1)[C@@H]1CCc2cc(F)ccc2O1 ; Cl]
(formula Ia)

ii. the corresponding l-Nebivolol hydrochloride

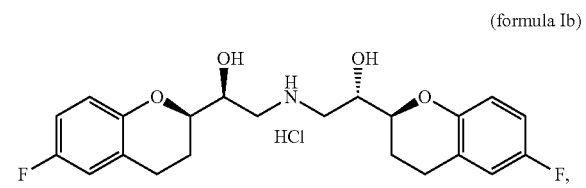 [SMILES: O[C@@H](CNC[C@H](O)[C@H]1CCc2cc(F)ccc2O1)[C@@H]1CCc2cc(F)ccc2O1 ; Cl]
(formula Ib)

or
iii. the corresponding mixture of d-Nebivolol hydrochloride and l-Nebivolol hydrochloride of formula IIa and IIb.

3. The process according to claim 1, wherein a racemic mixture of said protected d-Nebivolol hydrochloride IIa and said protected l-Nebivolol hydrochloride IIb is provided in step a, and wherein said hydrogenation of step b yields the corresponding racemic Nebivolol hydrochloride.

4. The process according to claim 1, wherein the amine protecting group P is

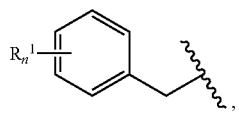

with n being 0, 1, 2, 3, 4 or 5 and each $R^1$ being selected independently from any other $R^1$ from F, Br, Cl, I or C- to C-alkyl.

5. The process according to claim 1, wherein a mixture of said protected d-Nebivolol hydrochloride IIa and said protected l-Nebivolol hydrochloride IIb is provided by
dissolving $n_{dp}$ mole of said protected d-Nebivolol hydrochloride IIa and $n_{lp}$ mole of said protected l-Nebivolol hydrochloride IIb in a precipitation solvent and
precipitating said mixture, wherein $n_{dp}$ is the molar amount of said protected d-Nebivolol hydrochloride IIa and nip is the molar amount of said protected l-Nebivolol hydrochloride IIb.

6. The process according to claim 1, wherein a racemic mixture of said protected d-Nebivolol hydrochloride compound and said protected l-Nebivolol hydrochloride compound is provided by dissolving 1 mole of said protected d-Nebivolol hydrochloride compound and 1 mole of said protected l-Nebivolol hydrochloride compound in a precipitation solvent and a subsequent precipitation of said racemic mixture.

7. The process according to claim 5, wherein said precipitation solvent is a THF/water mixture.

8. The process according to claim 5, wherein the protected Nebivolol hydrochloride IIa and IIb are dissolved of in equimolar amounts in a 8:1 to 3:1 THF/water mixture and subsequently crystallized at 0° C.

9. The process according to claim 1, wherein a Pd catalyst and cyclohexene or an alkylated cyclohexene or 1,4-cyclohexadiene is used in the hydrogenation of step b.

10. The process according to claim 9, wherein compounds of the formula II, IIIb or mixtures of IIa and IIb are dissolved in THF/water mixture (8:1 to 3:1) and treated with 5-10% Pd/C (5-10% w/w) under reflux in the presence of 50-100% w/w cyclohexene in the hydrogenation of step b.

11. The process according to claim 1, wherein said protected d-Nebivolol hydrochloride compound and said protected l-Nebivolol hydrochloride compound is provided by
  a. a coupling reaction of
    i. aminoalcohols of the general formula IIIa to IIId

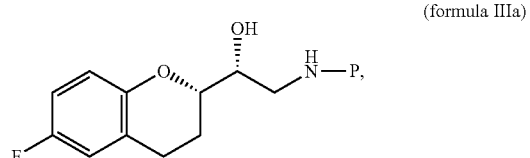
(formula IIIa)

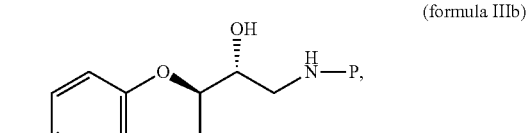
(formula IIIb)

(formula IIIc) or

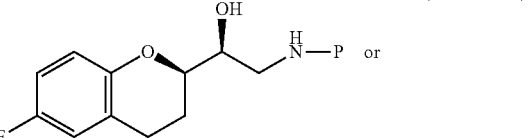
(formula IIId)

with P being an amine protecting group as defined previously,
    ii. with chloroalcohols of the general formula IVa to IVd

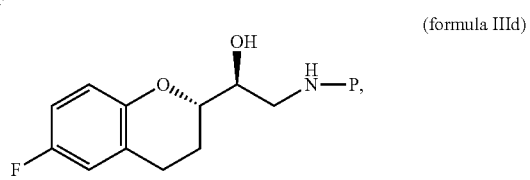
(formula IVa)

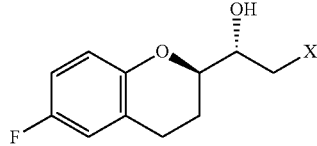
(formula IVb)

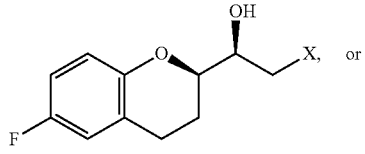
(formula IVc) or

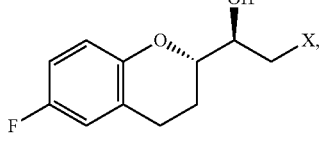
(formula IVd)

with X being a leaving group selected from Cl, Br, I, $OSO_2R$ or $OSO_2Ar$, with R being a $C_1$ to $C_6$-Alkyl and Ar being a phenyl, 4-nitrophenyl, or tolyl, providing a protected d-Nebivolol compound and a protected l-Nebivolol compound, which are produced by a coupling reaction of compound IIIa with compound IVb or compound IIIb with compound IVa and a coupling reaction of compound IIIc with compound IVd or compound IIId with compound IVc, and b. a subsequent treatment of said protected d-Nebivolol compound and said protected l-Nebivolol compounds with hydrochloric acid.

12. The process according to claim 11, wherein said aminoalcohols IIIa to IIId are provided by converting said chloroalcohols IVa to IVd to epoxide intermediates of the general formula Va to Vd

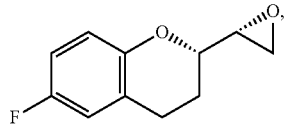
(formula Va)

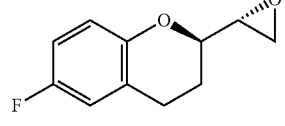
(formula Vb)

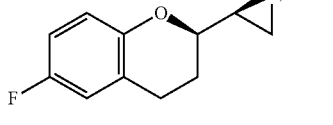
(formula Vc) or

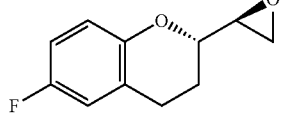
(formula Vd)

and a subsequent treatment with an amine of the formula HNP, with P being an amine protecting group as defined previously, wherein in particular said epoxide intermediates Va to Vd are not isolated prior to said treatment with the amine of the formula HNP.

13. The process according to 11, wherein said coupling reaction of said aminoalcohols IIIa to IIId with said chloroalcohols IVa to IVd is achieved by a conversion of said chloroalcohols IVa to IVd to said epoxide intermediates Va to Vd and a subsequent coupling with said aminoalcohols IIIa to IIId, wherein said epoxide intermediates Va to Vd are not isolated prior to said coupling with said aminoalcohols IIIa to IIId.

14. The process according to claim 11, wherein said conversion of the chloroalcohols IVa to IVd is achieved by an alkoxide base, a tertiary amine base, or an inorganic base selected from carbonates or bicarbonates and hydroxides, in a protic organic solvent, an alcohol solvent.

15. The process according to claim 1, wherein the amine of the formula HNP is benzylamine, wherein the treatment of said epoxide intermediates Va to Vd for providing said aminoalcohols IIIa to IIId comprises the addition of 1-10 eq of benzylamine.

\* \* \* \* \*